(12) United States Patent
Fisher et al.

(10) Patent No.: US 11,998,351 B2
(45) Date of Patent: Jun. 4, 2024

(54) TESTING FOR NEUROVASCULAR UNCOUPLING IN MULTIPLE SCLEROSIS USING SEQUENTIAL GAS DELIVERY VERSUS FIXED INSPIRED $CO_2$

(71) Applicant: THORNHILL SCIENTIFIC INC., North York (CA)

(72) Inventors: Joseph Arnold Fisher, Thornhill (CA); James Duffin, Toronto (CA); Olivia Sobczyk, Etobicoke (CA); David Mikulis, Oakville (CA)

(73) Assignee: THORNHILL SCIENTIFIC INC., North York (CA)

( * ) Notice: Subject to any disclaimer, the term of this patent is extended or adjusted under 35 U.S.C. 154(b) by 958 days.

(21) Appl. No.: 17/000,229

(22) Filed: Aug. 21, 2020

(65) Prior Publication Data
US 2021/0052220 A1    Feb. 25, 2021

Related U.S. Application Data

(60) Provisional application No. 62/891,070, filed on Aug. 23, 2019.

(51) Int. Cl.
*A61B 5/00* (2006.01)
*A61B 5/026* (2006.01)
*A61B 6/03* (2006.01)
*A61B 6/50* (2024.01)
*A61M 16/12* (2006.01)
(Continued)

(52) U.S. Cl.
CPC .......... *A61B 5/4884* (2013.01); *A61B 5/0263* (2013.01); *A61B 6/037* (2013.01); *A61B 6/507* (2013.01); *A61M 16/12* (2013.01); *G01R 33/4806* (2013.01); *A61B 5/14542* (2013.01); *A61M 2202/0208* (2013.01); *A61M 2202/0225* (2013.01)

(58) Field of Classification Search
CPC ..... A61B 5/4884; A61B 5/0263; A61B 6/037; A61B 6/507; A61M 2202/0208; A61M 2202/0225
See application file for complete search history.

(56) References Cited

U.S. PATENT DOCUMENTS

2010/0028441 A1* 2/2010 Watson ................... A61P 25/00
                                                           977/773
2016/0158481 A1* 6/2016 Klein .................. A61M 16/026
                                                           128/203.14

OTHER PUBLICATIONS

Sivakolundu, Dinesh K., et al. "Reduced arterial compliance along the cerebrovascular tree predicts cognitive slowing in multiple sclerosis: Evidence for a neurovascular uncoupling hypothesis." Multiple Sclerosis Journal (2019): 1352458519866605.
(Continued)

*Primary Examiner* — Joel F Brutus
(74) *Attorney, Agent, or Firm* — Perry + Currier Inc.

(57) ABSTRACT

An apparatus and method for assessing vascular compliance in subjects with multiple sclerosis using sequential gas delivery is provided. The apparatus includes a gas delivery device and a processor. The processor controls the gas delivery device to deliver a first and second gas during a single inspiration. The first gas contains a mixture of oxygen and carbon dioxide necessary to target an end-tidal concentration of the two gases. The second gas includes a concentration of carbon dioxide equal to the target end-tidal concentration of carbon dioxide.

16 Claims, 7 Drawing Sheets

(51) Int. Cl.
*G01R 33/48* (2006.01)
*A61B 5/145* (2006.01)

(56) References Cited

OTHER PUBLICATIONS

Fisher, Joseph A. "The CO2 stimulus for cerebrovascular reactivity: fixing inspired concentrations vs. targeting end-tidal partial pressures." Journal of Cerebral Blood Flow & Metabolism 36.6 (2016): 1004-1011.
Marshall, Olga, et al. "Impaired cerebrovascular reactivity in multiple sclerosis." JAMA neurology 71.10 (2014): 1275-1281.
Fisher, Joseph A et al. "Sequential gas delivery provides precise control of alveolar gas exchange." Respiratory Physiology & Neurobiology 225 (2016): 60-69. [Abstract].
Fierstra, J, et al. "Measuring cerebrovascular reactivity: what stimulus to use?." The Journal of physiology 591.23 (2013): 5809-5821.

* cited by examiner $$CBF\text{-based }CVR = \frac{CBF_{hypercapnia} - CBF_{normocapnia}}{etCO_{2,hypercapnia} - etCO_{2,normocapnia}}$$

Figure 1

$$BOLD\text{-based }CVR = \frac{BOLD_{hypercapnia} - BOLD_{normocapnia}}{etCO_{2,hypercapnia} - etCO_{2,normocapnia}}$$

Figure 2

$$\text{CBF-based CVR (layer)} = e^{ACI*layer}$$

Figure 3

$$\text{BOLD-based CVR (layer)} = e^{VCI*layer}$$

Figure 4

TESTING FOR NEUROVASCULAR UNCOUPLING IN MULTIPLE SCLEROSIS USING SEQUENTIAL GAS DELIVERY VERSUS FIXED INSPIRED $CO_2$

CROSS-REFERENCE TO RELATED APPLICATION(S)

This application claims the benefit of U.S. provisional application entitled AN IMPROVED TEST FOR NEUROVASCULAR UNCOUPLING IN MULTIPLE SCLEROSIS USING SEQUENTIAL GAS DELIVERY VERSUS FIXED INSPIRED CO2 having Ser. No. 62/891,070 by Fisher, filed Aug. 23, 2019 and incorporated by reference herein.

FIELD

The present invention is directed to a method and apparatus for assessing multiple sclerosis in a subject.

BACKGROUND

Multiple sclerosis (MS) is a disease of unknown etiology resulting in motor, visual, and sensory deficits. About 70% of patients with MS develop cognitive slowing with delays in response to verbal, visual challenges such as slowed working memory and verbal fluency.

One way to assess cognition in patients with MS is a response time (RT) cognitive test. In RT cognitive testing, patients are timed as they process and react to stimuli. Unfortunately, the testing process is time-consuming and stressful for the patients. It is also imprecise.

A testing method based on a physiologic variable has been suggested. In studies by Sivakolundu et al. and Marshall et al., a strong correlation was found between arterial compliance index (ACI) and RT in MS patients (Sivakolundu D K, West K L, Maruthy G B, Zuppichini M, Turner M P, Abdelkarim D, Zhao Y, Nguyen D, Spence J S, Lu H, Okuda D T, Rypma B. Reduced arterial compliance along the cerebrovascular tree predicts cognitive slowing in multiple sclerosis: Evidence for a neurovascular uncoupling hypothesis. Mult Scler 2019: 1352458519866605; Marshall O, Lu H, Brisset J C, Xu F, Liu P, Herbert J, Grossman R I, Ge Y. Impaired cerebrovascular reactivity in multiple sclerosis. JAMA Neurol 2014; 71: 1275-1281.). The studies indicate that in MS patients with delayed cognition, but not in healthy humans or those with MS but normal cognition, there is an abnormal pattern of change in blood flow in the first 4 concentric layers of the brain cortex, each about 1.25 millimeters wide.

Sivakolundu et al. administered a vasoactive stimulus of increased inspired $CO_2$ consisting of breathing air for 4 min then inhaling 5% $CO_2$ in air for 6 min. They measured cerebral blood flow (CBF) and Blood Oxygen Level Dependent (BOLD) signal which is also a surrogate for blood flow. Cerebrovascular reactivity (CVR) may be calculated using CBF and BOLD signal for each layer according to the formulas in FIGS. 1 and 2.

As the CVR may be successively reduced in each layer, they measured the rate of reduction as a decay constant. The rate of decay is described by a rate constant for the arterial (ACI) and venous (VCI) blood, as shown in the formulas in FIGS. 3 and 4. The CVR is each layer of the cerebral cortex is plotted in graphs from Sivakolundu et al., shown in FIGS. 5 and 6. These graphs show the reductions in CVR by layer for healthy subjects 2, cognitively normal MS subjects 3, and cognitively slow MS subjects 4.

There are a number of limitations to the test suggested by Sivakolundu et al. The sensitivity of the test is dependent on the test variability between subjects and the test-test variability within a subject. The magnitude of the variability of the vasoactive stimulus adds the variability of the ACI and degrades the sensitivity of the test. The inhalation of a fixed gas as a vasoactive stimulus is highly variable as there can be only wide constraints, or poor precision, as to the arterial partial pressure of $CO_2$ ($PaCO_2$) and the timing of changes to $PaCO_2$. With poor repeatability of the test, it is difficult to designate a precise normal range and have confidence in designating a threshold between a normal and abnormal test.

SUMMARY

It is an aspect of the present disclosure to provide a method of providing a vasoactive stimulus to a subject with MS to assess vascular compliance with regard to MS-related cognition.

The above aspects can be attained by delivering a first and second gas to the subject while the subject is inhaling.

The volume of the first gas is less than a tidal volume minus anatomical dead space. The first gas contains a concentration of oxygen require to meet the respiratory need of the subject and to target an end-tidal partial concentration of oxygen. The first gas also contains a concentration of carbon dioxide required to target an end-tidal concentration of carbon dioxide and thereby provide a vasoactive stimulus to the subject to assess vascular compliance with regard to MS-related cognition of the subject.

The second gas contains a concentration of carbon dioxide approximately equal to the target end-tidal concentration of carbon dioxide, or if at resting state, equilibrated with an arterial partial pressure of carbon dioxide of the subject.

It is a further aspect of the present disclosure to provide an apparatus for providing a vasoactive stimulus to a subject with MS to assess vascular compliance with regard to MS-related cognition of the subject.

The apparatus includes a gas delivery device and a processor connected to the gas delivery device.

The processor is configured to control the gas delivery device to deliver a first gas to the subject while the subject is inhaling. The volume of the first gas is less than a tidal volume minus anatomical dead space. The first gas contains a concentration of oxygen require to meet the respiratory need of the subject and to target an end-tidal partial concentration of oxygen. The first gas also contains a concentration of carbon dioxide required to target an end-tidal concentration of carbon dioxide.

The process is further configured to control the gas delivery device to deliver a second gas to the subject in the same inhalation. The second gas contains a concentration of carbon dioxide approximately equal to the target end-tidal concentration of carbon dioxide, or if at resting state, equilibrated with an arterial partial pressure of carbon dioxide of the subject.

It is a yet further aspect of the present disclosure to provide the use of sequential gas delivery, including delivery of a gas containing carbon dioxide, to test for neurovascular uncoupling in a subject with MS.

It is a still further aspect of the present disclosure to provide the use of sequential gas delivery, including delivery of a gas containing carbon dioxide, to determine vascular compliance in a subject with MS.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a formula for calculating the CVR using CBF.
FIG. 2 is a formula for calculating the CVR using BOLD.
FIG. 3 is a formula for calculating the rate of decay of CVR in arterial blood.
FIG. 4 is a formula for calculating the rate of decay of CVR in venous blood.

DETAILED DESCRIPTION

The present invention will be described with respect to a method apparatus for providing a vasoactive stimulus to a subject with MS to assess vascular compliance with regard to MS-related cognition. According to the method, the subject sequentially inhales compositions of gas including carbon dioxide and oxygen that are calculated to attain a targeted $P_{ET}CO_2$. Vascular compliance is then assessed in the patient.

This method and apparatus offer a number of advantages over the prior art method in which the $P_{ET}CO_2$ is highly variable and the true physiologic independent variable ($PaCO_2$) is unknown. In the method disclosed herein, $P_{ET}CO2$ is more precisely controlled and is approximately equal to $PaCO_2$. By targeting a particular value of $P_{ET}CO_2$, it is possible to designate a normal range for vascular compliance and determine a threshold between a normal and abnormal test result. Furthermore, the method allows the $PaCO_2$ to be changed from one targeted value to a second targeted value within two breaths. In contrast, the timing of $P_{ET}CO_2$ changes in the prior art method was determined by the functional residual capacity (FRC) and respiratory response of the subject, both of which are unknown and outside of the control of the tester.

The $PaCO_2$ of the subject may be controlled with a sequential gas delivery (SGD) device. For example, RespirAct™ (Thornhill Medical Inc., Toronto, Canada) may be used in this method, although the method is not particularly limited to the RespirAct™ system.

Figure 5:
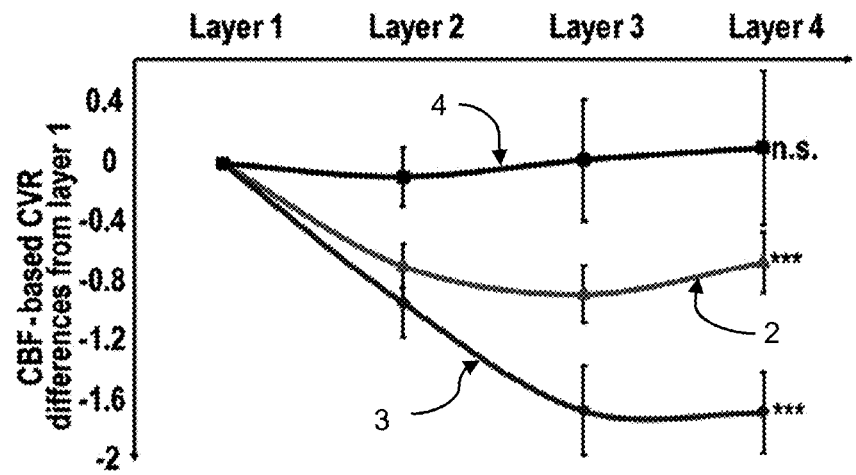
FIG. 5 is a graph describing CBF-based CVR in a first, second, third, and fourth layer of the cerebral cortex for healthy controls, cognitively normal MS, and cognitively slow MS.
Figure 6:
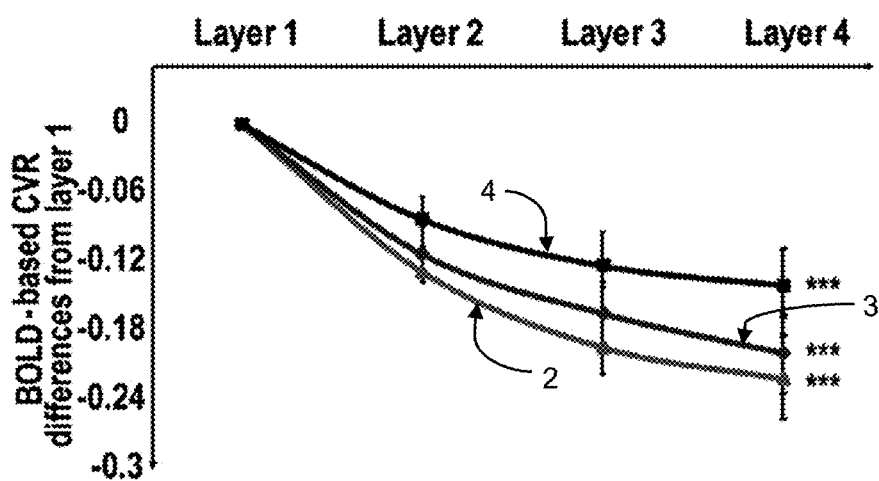
FIG. 6 is a graph describing BOLD-based CVR in a first, second, third, and fourth layer of the cerebral cortex for healthy controls, cognitively normal MS, and cognitively slow MS.
Figure 7:
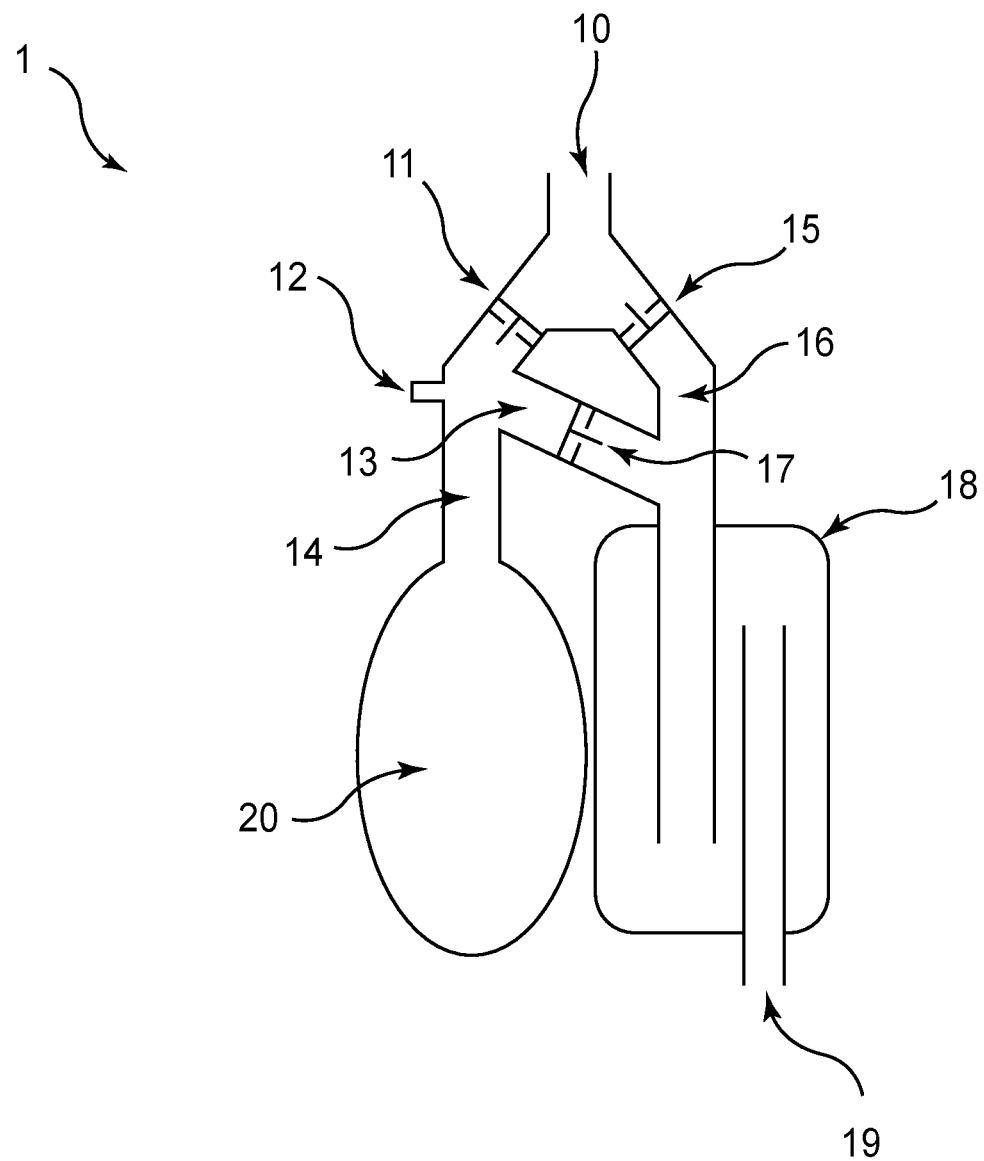
FIG. 7 is a schematic diagram of a sequential gas delivery device.

FIG. 7 shows a schematic diagram of a SGD device at 1, as taught by Fisher et al. in U.S. Pat. No. 6,622,725. The SGD device 1 includes a subject port 10 that provides gases to the subject. The flow of gases through the subject port 10 may be controlled by an inspiratory valve 11. The inspiratory valve may be a type of valve that opens in response to a subject inspiring and closes in response to the subject exhaling, for example, a one-way check. The inspired gas may be provided from the inlet 12, the by-pass limb 13, or the inspiratory limb 14. All three sources of gas are in communication with the subject port 10 when the inspiratory valve 11 is open. When the subject expires, the inspiratory valve 11 closes and an expiratory valve 15 opens. The expiratory valve 15 may be a one-way check valve. The expired gas flows through the expiratory limb 16 but cannot flow through the by-pass limb 13 due to a cross-over valve 17, which remains closed as the subject expires. Instead, the expired gas flows into the expiratory reservoir 18. The expiratory reservoir may have a fixed volume such that excess gas is forced out through the outlet 19. An inspiratory reservoir 20 is connected to the inspiratory limb 14. In contrast to the expiratory reservoir 18, the inspiratory reservoir 20 does not have a fixed volume and may expand and contract to hold different volumes of gas.

Figure 8:
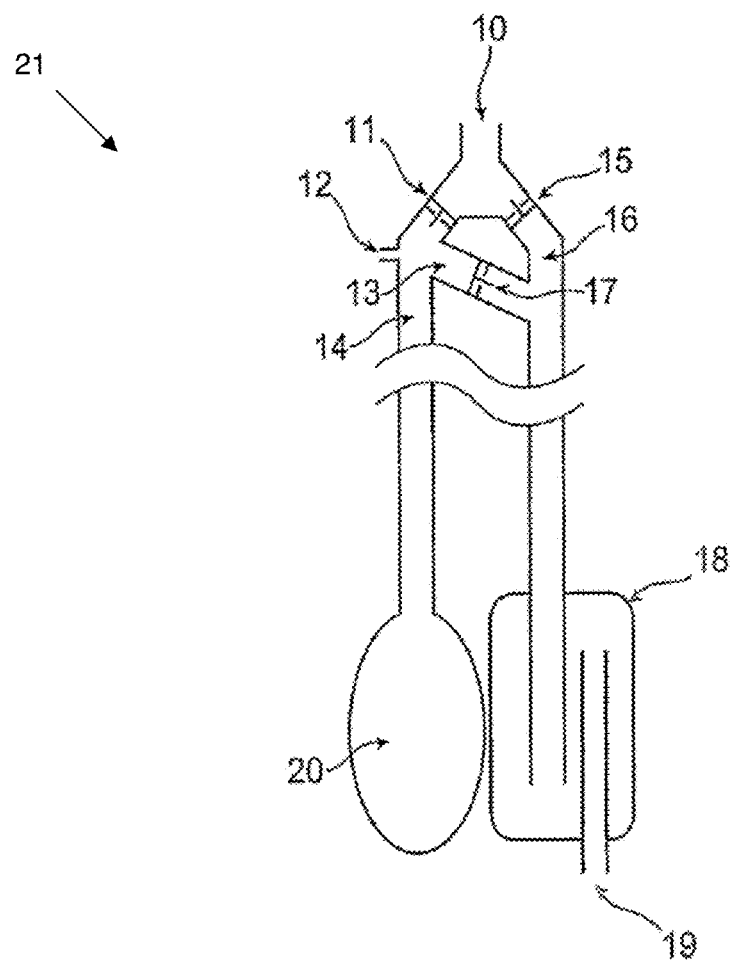
FIG. 8 is a schematic diagram of the sequential gas delivery device in FIG. 7 wherein the reservoirs are remote from the subject.

Turning now to FIG. 8, a schematic diagram of the sequential gas delivery device from FIG. 7 is shown at 21. In this implementation, the reservoirs 18, 20 are remote from the subject.

When a subject is being assessed for MS, the subject may be instructed to breathe through subject port 10, which may be connected to a ventilation mask or mouthpiece. The SGD device 1 operates such that a first gas may be inspired during a first part of a subject's inspiration and a second gas may be inspired during a second part of a subject's inspiration.

Figure 9:
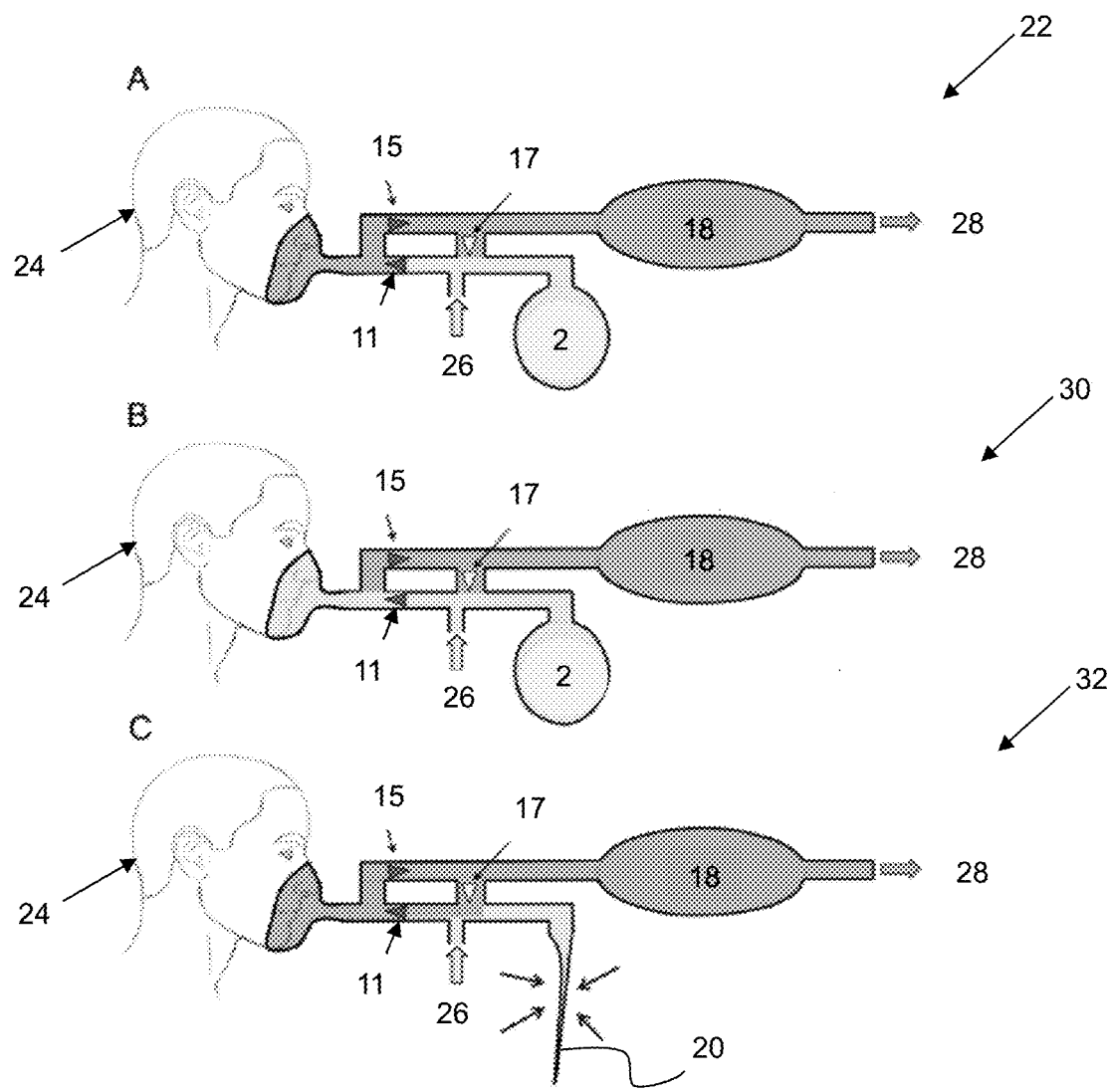
FIG. 9A is a schematic diagram of a subject exhaling into the sequential gas delivery device of FIG. 7.
FIG. 9B is a schematic diagram of a first part inhalation into the sequential gas delivery device of FIG. 7.
FIG. 9C is a schematic diagram of a second part of inhalation into the sequential gas delivery device of FIG. 7.

FIGS. 9A to 9C show schematic diagrams of a subject 24 exhaling and inhaling through the SGD device 1. In the example shown in FIGS. 9A to 9C, the second gas 28 is a previously exhaled gas.

First, FIG. 9A shows the subject expiring the second gas 28 into the subject port 10. The second gas 28 passes through the expiratory valve 15 and through the expiratory limb 16 to fill the expiratory reservoir 18. Any excess of the second gas 28 may be expelled through the outlet 19. As the subject 24 exhales, the first gas 26 may be provided through the inlet 12 to fill the inspiratory reservoir 20.

Next, FIG. 9B shows a schematic diagram 30 of a first part inhalation into the SGD device 1. When the subject inhales through the subject port 10, the inspiratory valve 11 opens and the first gas 26 from the inspiratory reservoir 20 may flow through the inspiratory limb 14 to be delivered to the subject through the subject port 10.

The first gas 26 contains a concentration of oxygen required to meet the respiratory need of the subject and to target an end-tidal concentration of oxygen. The first gas 26 contains a concentration of carbon dioxide required to target a $P_{ET}CO_2$. The first gas 26 is provided in a volume that is less than the subject's tidal volume, minus the subject's anatomical dead space. Consequently, the subject 24 will continue to inspire after the quantity of the first gas 26 contained in the inspiratory reservoir 20 has been depleted.

On the second part of the subject's inspiration and after the first gas has been delivered to the subject, a second gas is delivered to the subject. FIG. 9C shows a schematic diagram 32 of a second part of inhalation into the SGD device 1. In the system shown in FIGS. 9A to 9C, the second gas 28 is provided by the expiratory reservoir 18 and passes through the cross-over limb, through the inspiratory limb, and out through the subject port.

In the example shown in FIGS. 9A to 9C, the second gas 28 is the expired gas, although in other implementations, the second gas 28 may be a gas mixture provided by a gas blender. Regardless of the source of the second gas 28, the second gas 28 contains a concentration of carbon dioxide approximately equal to the target $P_{ET}CO_2$. Alternatively, if the subject 24 is in a resting state, the concentration of carbon dioxide may be equilibrated with a $PaCO_2$ in the subject 24.

Figure 10:
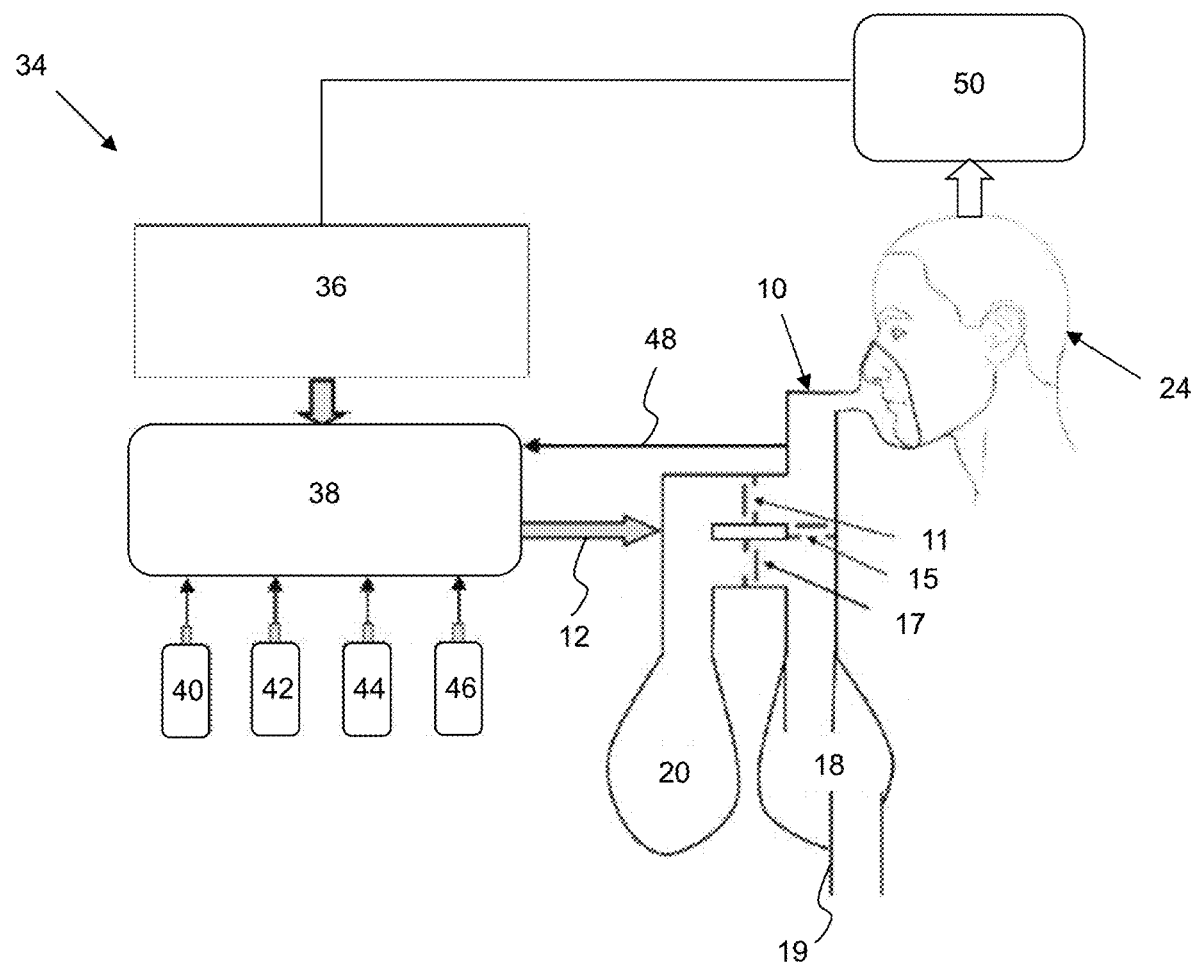
FIG. 10 is a schematic diagram of another sequential gas delivery device.

Precise compositions of the first gas may be provided to the gas delivery device with a gas blender. FIG. 10 shows a schematic diagram of an SGD device 34 that includes a processor 36 and a gas blender 38. The gas blender 38 may be in communication with the inlet 12. One or more gas sources 40, 42, 44, 46 may provide gases to the gas blender 38. The gases may include, but are not limited to, carbon dioxide, oxygen, and nitrogen. One or more of the gases may be selected to induce a vasoactive response in the subject. The gases may be provided in quantities that are controlled by the processor 36.

The processor 36 may include a central processing unit (CPU), a microcontroller, a microprocessor, a processing core, a field-programmable gate array (FPGA), an application-specific integrated circuit (ASIC), or a similar device capable of executing instructions. The processor may be connected to and cooperate with a non-transitory machine-readable medium (not shown) that stores instructions and data.

The non-transitory machine-readable medium may include an electronic, magnetic, optical, or other physical storage device that encodes the instructions. The medium may include, for example, random access memory (RAM), read-only memory (ROM), electrically-erasable programmable read-only memory (EEPROM), flash memory, a storage drive, an optical device, or similar.

Instructions may be provided to carry out the functionality and methods described herein. Instructions may be directly executed, such as a binary file, and/or may include interpretable code, bytecode, source code, or similar instructions that may undergo additional processing to be executed. The instructions may dictate the quantities of gas provided to the subject 24 by the gas blender 38 in order to achieve a target $P_{ET}CO_2$.

In this system, $P_{ET}CO_2$ is approximately equal to $PaCO_2$. Therefore, $P_{ET}CO_2$ may be measured as an approximation of the value of $PaCO_2$ in the subject 24. In some implementations, the subject's actual $PaCO_2$ may be within 2 mmHg of the targeted $PaCO_2$. In other implementations, the subject's actual $PaCO_2$ may be within 1 mmHg of the targeted $PaCO_2$.

The gas blender 38 may include a carbon dioxide analyzer and/or an oxygen analyzer, which are in communication 48 with the subject port 10. The carbon dioxide analyzer may measure the subject's $P_{ET}CO_2$ at the end of each breath by the subject 24. The measured $P_{ET}CO_2$ may be transmitted from the gas blender 38 to the processor 36. The measured $P_{ET}CO_2$ may be stored on the non-transitory machine-readable medium.

The processor 36 may transmit instructions for the gas blender 38 to target one $P_{ET}CO_2$ for a first series of inspirations. In some examples, the number of inspirations in the first series of inspirations is two or three. When the processor 36 receives a transmission from the gas blender 38 indicating that the first targeted $P_{ET}CO_2$ has been reached, the processor 36 may instruct the gas blender to provide a composition of the first gas appropriate to targeting a different $P_{ET}CO_2$ for a further series of inspirations by the subject 24. The targeted $P_{ET}CO_2$ may be reached within two or three inspirations by the subject 24.

The first and second targeted $P_{ET}CO_2$ values may be input into the processor 36 by a user. In some implementations, the processor 36 may be programmed to implement two predetermined targeted $P_{ET}CO_2$ values that are stored on the non-transitory machine-readable medium. In further implementations, the processor 36 may be programmed to calculate a first and second targeted $P_{ET}CO_2$ value based on physiologic attributes of the subject 24.

A number of different values are possible for the two $P_{ET}CO_2$ targets. For example, a $P_{ET}CO_2$ associated with normocapnia may be targeted for a number of inspirations and then a $P_{ET}CO_2$ associated with hypercapnia may be targeted for a further number of inspirations. However, the steps do not need to be performed in that order. In some implementations, a $P_{ET}CO_2$ associated with hypercapnia may be targeted for a number of inspirations and then a $P_{ET}CO_2$ associated with normocapnia may be targeted for a further number of inspirations. The two targeted $P_{ET}CO_2$ values do not necessarily need to be associated with normocapnia and hypercapnia, as long as the two targeted $P_{ET}CO_2$ are sufficiently different to elicit a vasoactive response in the subject 24. For instance, one of targeted values may be associated with hypocapnia. In another example, both of the targeted values may be within a range of values associated with one of normocapnia, hypercapnia, or hypocapnia.

The carbon dioxide acts as a vasoactive stimulus for studying the vascular compliance of the subject 24. A sensor 50 may measure blood flow in the subject's brain when the first targeted $P_{ET}CO_2$ is reached and re-measure blood flow in the subject's brain when the second targeted $P_{ET}CO_2$ is reached. The sensor 50 may transmit the first and second measured blood flow to the processor 36.

The sensor 50 that measures blood flow in the subject's brain may be selected from a number of suitable devices. For example, the sensor 50 may be a magnetic resonance imaging (MRI) scanner or a positron emission tomography (PET) scanner. If an MRI scanner is used, blood flow may be quantified according to blood oxygen level dependent (BOLD) imaging techniques. If a PET scanner is used, blood flow may be quantified according to cerebral blood flow (CBF) imaging techniques. The blood flow measured at the first and second targeted $P_{ET}CO_2$ may be transmitted to the processor 36.

The change in blood flow measured at each $P_{ET}CO_2$ may be indicative of multiple-sclerosis related cognition. The processor 36 may calculate the cardiovascular reactivity (CVR) of the subject 24 according to the formulas in FIGS. 1 and 2:

In some implementations, the sensor 50 may be adapted to measure blood flow in a single layer of the subject's cerebral cortex. In other implementations, the sensor 50 may be adapted to measure blood flow in a plurality of layers of the subject's cerebral cortex.

The processor 36 may be further configured to calculate a rate of decay for each layer of the subject's cerebral cortex. The rate of decay may be described by a rate constant for the ACI and VCI according to the formulas in FIGS. 3 and 4.

Figure 11:
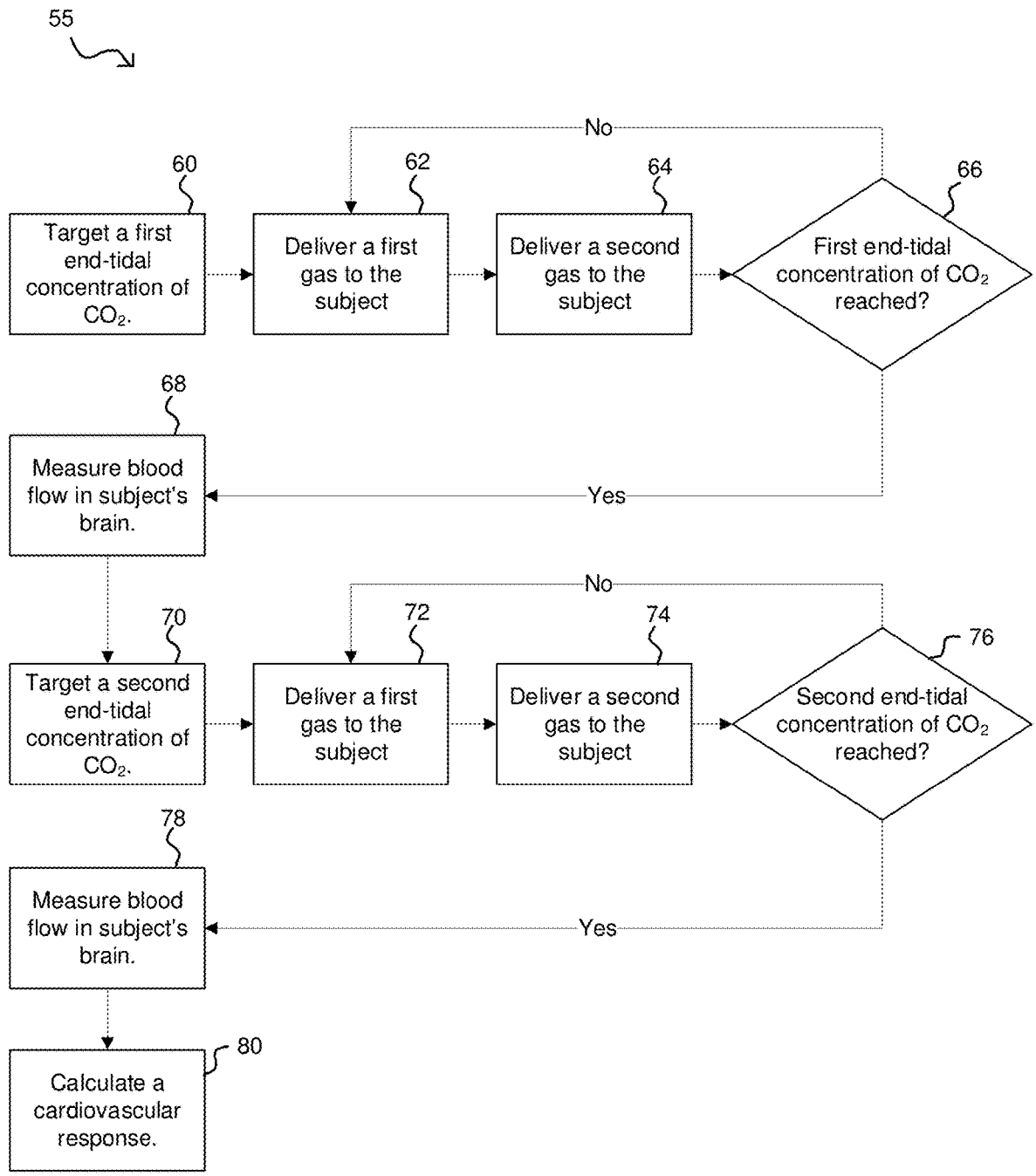
FIG. 11 is a flowchart showing a method of assessing vascular compliance in a subject with MS.

FIG. 11 shows a flowchart at 55 illustrating a method of assessing vascular compliance in a subject with MS. The blocks in the flowchart may be encoded as instructions and stored in a non-transitory computer-readable memory for execution by a processor.

The method may begin at block 60 with targeting a first $P_{ET}CO_2$ in a subject with MS. The first $P_{ET}CO_2$ may be a pre-determined value or it may be calculated by a processor. Block 60 may be implemented with instructions to control a gas delivery device to target the first $P_{ET}CO_2$.

Next, a first gas is delivered to the subject at block 62. The first gas is provided to the subject in a volume that is less than the subject's tidal volume minus the subject's anatomical dead space. The first gas contains both oxygen and carbon dioxide, each provided in sufficient concentrations to meet the respiratory needs of the subject and target the first $P_{ET}CO_2$. Block 62 may be implemented with instructions to control a gas delivery device.

After delivering a first gas to the subject, a second gas is delivered to the subject at block 64 during the same inspiration. The second gas may contain a concentration of carbon dioxide approximately equal to the first $P_{ET}CO_2$. Alternatively, if the subject is at resting state, the second gas may contain a concentration of carbon dioxide equilibrated with the subject's $PaCO_2$. Block 64 may be implemented with instructions to control a gas delivery device.

The next step at block 66 is to determine whether the first $P_{ET}CO_2$ has been reached. Block 66 occurs as the subject expires and the subject's $P_{ET}CO_2$ is measured. The processor may be instructed to compare the subject's $P_{ET}CO_2$ to the value of the first $P_{ET}CO_2$. If the subject's $P_{ET}CO_2$ is not equal or approximately equal to the first $P_{ET}CO_2$, the determination is NO and the method returns to block 62. Blocks 62, 64, and 66 may be repeated a number of times over a series of inspirations by the patient. When the subject's $P_{ET}CO_2$ is equal or approximately equal to the first $P_{ET}CO_2$, the determination is YES and the method proceeds to block 68.

At block 68, the blood flow in the subject's brain may be measured. Block 68 may be implemented with instructions to a sensor and the measured blood flow may be stored in a memory. The blood flow may be measured in a plurality of layers of the subject's brain. In order to ensure that the measured blood flow corresponds with the targeted first $P_{ET}CO_2$, block 68 may be implemented almost immediately after block 66. In some implementations, block 68 may be implemented simultaneously with block 66. For methods that implement blocks 66 and 68 simultaneously, the blood flow measurement(s) may not be stored in memory, or the blood flow measurement(s) may be erased from a memory, if the determination at block 66 is NO.

At block 70, a second $P_{ET}CO_2$ may be targeted in a subject with MS. The second $P_{ET}CO_2$ may be a pre-determined value or it may be calculated by a processor. The second $P_{ET}CO_2$ is different from the first $P_{ET}CO_2$. For instance, one of the targeted $P_{ET}CO_2$ values may be correlated with hypercapnia in the subject and the other targeted $P_{ET}CO_2$ value may be correlated with normocapnia. Block 60 may be implemented with instructions to control a gas delivery device to target the first $P_{ET}CO_2$.

Then at block 72, a first gas is delivered to the subject. The first gas is provided to the subject in a volume that is less than the subject's tidal volume minus the subject's anatomical dead space. The first gas contains both oxygen and carbon dioxide, each provided in sufficient concentrations to meet the respiratory needs of the subject and target the second $P_{ET}CO_2$. Block 72 may be implemented with instructions to control a gas delivery device.

After delivering a first gas to the subject, a second gas is delivered to the subject at block 74 during the same inspiration. The second gas may contain a concentration of carbon dioxide approximately equal to the second $P_{ET}CO_2$. Alternatively, if the subject is at resting state, the second gas may contain a concentration of carbon dioxide equilibrated with the subject's $PaCO_2$. Block 74 may be implemented with instructions to control a gas delivery device.

The next step at block 76 is to determine whether the second $P_{ET}CO_2$ has been reached. Block 76 occurs as the subject expires and the subject's $P_{ET}CO_2$ is measured. The processor may be instructed to compare the subject's $P_{ET}CO_2$ to the value of the second $P_{ET}CO_2$. If the subject's $P_{ET}CO_2$ is not equal or approximately equal to the second $P_{ET}CO_2$, the determination is NO and the method returns to block 72. Blocks 72, 74, and 76 may be repeated a number of times over a series of inspirations by the patient. When the subject's $P_{ET}CO_2$ is equal or approximately equal to the second $P_{ET}CO_2$, the determination is YES and the method proceeds to block 78.

At block 78, the blood flow in the subject's brain may be measured. Block 78 may be implemented with instructions to a sensor and the measured blood flow may be stored in a memory. The blood flow may be measured in a plurality of layers of the subject's brain. In order to ensure that the measured blood flow corresponds with the second $P_{ET}CO_2$, block 78 may be implemented almost immediately after block 66. In some implementations, block 78 may be implemented simultaneously with block 66. For methods that implement blocks 76 and 78 simultaneously, the blood flow measurements(s) may not be stored in memory, or the blood flow measurements(s) may be erased from a memory, if the determination at block 76 is NO.

Finally, at block 80, a cardiovascular response is calculated. Block 80 may be implemented with instructions to a processor to calculate the cardiovascular response based on the first $P_{ET}CO_2$, the blood flow in the subject's at the first $P_{ET}CO_2$, the second $P_{ET}CO_2$, and the blood flow in the subject's brain at the second $P_{ET}CO_2$. If blood flow was measured in a plurality of layers of the subject's brain, a cardiovascular response may be calculated for each of those layers. Further, block 80 may be implemented with instructions to a processor to calculate the rate of decay of the cardiovascular response with respect to the plurality of layers of the subject's brain. The calculations implemented at block 80 may be indicative of neurovascular uncoupling associated with MS.

The methods and apparatus described above may be used to assess the MS-related cognition of a subject with MS. The methods and apparatus may also be used to assess neurovascular uncoupling a subject with MS. The methods and apparatus may further be used to assess vascular compliance in a subject with MS.

MS testing using sequential gas delivery may be highly repeatable. By collecting data from subjects with and without MS, it may be possible to designate a threshold between a normal test and an abnormal test. Data may be collected from healthy subjects, subjects with cognitively normal MS, and subjects with cognitively slow MS, and standard values or ranges of values may be determined for each category of subjects.

The repeatability of this test arises from the capability of an SGD device to implement any pre-determined $P_{ET}CO_2$ value. Using an SGD system, a targeted $P_{ET}CO_2$ may be achieved, independent of the rate or pattern of breathing of the subject. Additionally, the process is rapid. A targeted $P_{ET}CO_2$ may be reached within two breaths and a second targeted $P_{ET}CO_2$ value may be reached within another two breaths.

The repeatability also arises from the precision of targeting a $PaCO_2$ value. Using the SGD system described above, the subject's $PaCO_2$ is approximately equal to the $P_{ET}CO_2$ value measured by the device. Therefore, the test results accurately reflect the physiologic conditions in the subject's vascular system.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

We claim:

1. A method of assessing a subject with multiple sclerosis comprising:
   targeting a first end-tidal concentration of carbon dioxide for a first series of repeated inspirations by the subject, and targeting a second end-tidal concentration of carbon dioxide for a second series of repeated inspirations by the subject, wherein targeting the first and second end-tidal concentrations of carbon dioxide comprises:
      during an inspiration by a subject with multiple sclerosis, delivering a first gas to the subject, the first gas provided in a volume that is less than a tidal volume minus an anatomical dead space, the first gas containing a concentration of oxygen to meet a respiratory need of the subject and to target an end-tidal partial concentration of oxygen, the first gas further containing a concentration of carbon dioxide to target the first or second end-tidal concentration of carbon dioxide and thereby provide a vasoactive stimulus to the subject to assess vascular compliance with regard to multiple sclerosis-related cognition of the subject; and
      during the same inspiration and after delivering the first gas to the subject, delivering a second gas to the subject, wherein the second gas contains a concentration of carbon dioxide approximately equal to the target end-tidal concentration of carbon dioxide or, if at a resting state, equilibrated with an arterial partial pressure of carbon dioxide of the subject;
   when the first end-tidal concentration of carbon dioxide is reached, measuring blood flow in the subject's brain;
   when the second end-tidal concentration of carbon dioxide is reached, measuring blood flow in the subject's brain; and
   calculating a cardiovascular response using a difference between the blood flow measured at the first and second end-tidal concentrations of carbon dioxide.

2. The method of claim 1, further comprising delivering the first and second gases during repeated inspirations by the subject.

3. The method of claim 1, wherein the second gas includes rebreathed gas exhaled by the subject during an expiration prior to the inspiration.

4. The method of claim 1 further comprising:
   selecting the first end-tidal concentration of carbon dioxide to induce normocapnia in the subject; and
   selecting the second end-tidal concentration of carbon dioxide to induce hypercapnia in the subject.

5. The method of claim 1 further comprising measuring blood flow using one or both of cerebral blood flow imaging and blood oxygen level dependent signal.

6. The method of claim 1 further comprising measuring blood flow in a plurality of layers of the subject's cerebral cortex.

7. The method of claim 1 further comprising calculating the vascular compliance using the cardiovascular response.

8. An apparatus for providing a vasoactive stimulus to a subject with multiple sclerosis to assess vascular compliance with regard to multiple sclerosis-related cognition of the subject, the apparatus comprising:
   (a) a gas delivery device; and
   (b) a processor connected to the gas delivery device,
   wherein the processor is configured to:
      control the gas delivery device to target a first end-tidal concentration of carbon dioxide for a first series of repeated inspirations by the subject, and control the gas delivery device to target a second end-tidal concentration of carbon dioxide for a second series of repeated inspirations by the subject, wherein targeting the first and second end-tidal concentrations of carbon dioxide comprises:
         during an inspiration by a subject with multiple sclerosis, controlling the gas delivery device to deliver a first gas to the subject, the first gas provided in a volume that is less than a tidal volume minus an anatomical dead space, the first gas containing a concentration of oxygen to meet a respiratory need of the subject and to target an end-tidal partial concentration of oxygen, the first gas further containing a concentration of carbon dioxide to target an end-tidal concentration of carbon dioxide; and
         during the same inspiration and after delivering the first gas to the subject, controlling the gas delivery device to deliver a second gas to the subject, wherein the second gas contains a concentration of carbon dioxide approximately equal to the target end-tidal concentration of carbon dioxide or, if at a resting state, equilibrated with an arterial partial pressure of carbon dioxide of the subject,
      when the first end-tidal concentration of carbon dioxide is reached, control a sensor to measure blood flow in the subject's brain;
      when the second end-tidal concentration of carbon dioxide is reached, control the sensor to measure blood flow in the subject's brain; and
      calculate a cardiovascular response using the difference between the blood flow measured at the first and second end-tidal concentrations of carbon dioxide.

9. The apparatus of claim 8, the processor further configured to control the gas delivery device to deliver the first and second gases during repeated inspirations by the subject.

10. The apparatus of claim 8 wherein the second gas includes rebreathed gas exhaled by the subject during an expiration prior to the inspiration.

11. The apparatus of claim 8, the processor further configured to:
   select the first end-tidal concentration of carbon dioxide to induce normocapnia in the subject; and
   select the second end-tidal concentration of carbon dioxide to induce hypercapnia in the subject.

12. The apparatus of claim 8, the processor further configured to control the sensor to measure blood flow using one or both of cerebral blood flow imaging and blood oxygen level dependent signal.

13. The apparatus of claim 8, the processor further configured to control the sensor to measure blood flow in a plurality of layers of the subject's cerebral cortex.

14. The apparatus of claim 8, the processor further configured to calculate vascular compliance using the cardiovascular response.

15. A method of using sequential gas delivery to test for neurovascular uncoupling in a subject with multiple sclerosis, the method comprising:
- targeting a first end-tidal concentration of carbon dioxide for a first series of repeated inspirations by the subject;
- when the first end-tidal concentration of carbon dioxide is reached, measuring blood flow in the subject's brain;
- targeting a second end-tidal concentration of carbon dioxide for a second series of repeated inspirations by the subject;
- when the second end-tidal concentration of carbon dioxide is reached, measuring blood flow in the subject's brain; and
- calculating a cardiovascular response using a difference between the blood flow measured at the first and second end-tidal concentrations of carbon dioxide.

16. A method of using sequential gas delivery to determine vascular compliance in a subject with multiple sclerosis; the method comprising:
- targeting a first end-tidal concentration of carbon dioxide for a first series of repeated inspirations by the subject;
- when the first end-tidal concentration of carbon dioxide is reached, measuring blood flow in the subject's brain;
- targeting a second end-tidal concentration of carbon dioxide for a second series of repeated inspirations by the subject;
- when the second end-tidal concentration of carbon dioxide is reached, measuring blood flow in the subject's brain; and
- calculating a cardiovascular response using a difference between the blood flow measured at the first and second end-tidal concentrations of carbon dioxide.

\* \* \* \* \*